United States Patent [19]

Miller et al.

[11] Patent Number: 4,611,073

[45] Date of Patent: Sep. 9, 1986

[54] PREPARATION OF HIGHER SILICON CARBOXYLATES IN IMPROVED YIELDS USING AN INERT GAS

[75] Inventors: Richard F. Miller, Humble; Marilyn W. Blaschke, Pearland, both of Tex.

[73] Assignee: Atlantic Richfield Company, Los Angeles, Calif.

[21] Appl. No.: 814,127

[22] Filed: Dec. 27, 1985

[51] Int. Cl.$^4$ .............................................. C07F 7/02
[52] U.S. Cl. ................... 556/442; 260/404.8; 260/413
[58] Field of Search ............... 556/442; 260/404.8, 260/413

[56] References Cited

U.S. PATENT DOCUMENTS

| | | | |
|---|---|---|---|
| 2,017,000 | 10/1935 | Hintermaier | 556/442 X |
| 2,566,347 | 9/1951 | MacKenzie | 556/442 |
| 2,634,285 | 4/1953 | Rust et al. | 556/442 |
| 2,866,800 | 12/1958 | MacKenzie et al. | 556/442 |

*Primary Examiner*—Paul F. Shaver
*Attorney, Agent, or Firm*—Coleman R. Reap

[57] ABSTRACT

Silicon tetracarboxylates of higher acids are prepared by contacting silicon tetracarboxylates of lower fatty acids with higher fatty acids at a temperature sufficiently high to vaporize the lower fatty acid by-product. The reaction may be carried out in the presence of an inert gas, if desired.

13 Claims, No Drawings

PREPARATION OF HIGHER SILICON CARBOXYLATES IN IMPROVED YIELDS USING AN INERT GAS

FIELD OF THE INVENTION

Catalysts used in cracking hydrocarbons can become contaminated and poisoned by accumulation in the catalyst of metal poisons such as nickel, vanadium, iron, copper and cobalt which are present in the hydrocabon feedstocks. The detrimental effects of these metals can be mitigated and reversed by use of certain organo-silicon compounds as metal passivators. Among those organo-silicon compounds are silicon tetracarboxylates. The present invention is an improved method of preparing silicon carboxylates in exceedingly high yields.

BACKGROUND OF THE INVENTION

Certain silicon compounds are known to be used to treat those cracking catalysts conventionally employed in the catalytic cracking of hydrocarbons for the production of gasoline, motor fuel, blending components and light distillates. These conventional cracking catalysts generally contain silica, or silica-alumina. Such materials are frequently associated with zeolite materials. These zeolitic materials can be used as naturally occurring, or they can be modified by conventional ion exchange methods to attach metallic ions which improve the activity of the catalyst.

While the presence on the catalyst of certain metals can be beneficial, the presence of others is detrimental. It is well known that varying amounts of metals such as nickel, vanadium and iron cause deterioration of the cracking catalyst during the cracking process. In fact, some oils contain these metals in such a high concentration that they cannot be economically catalytically cracked into gasoline and other fuels. The metals accumulate on the cracking catalyst and cause increased hydrogen production and coke laydown on the cracking catalyst, thereby adversely affecting the yield of desired products.

The production of silicon tetracarboxylates by the direct reaction between silicon dioxide and the desired higher carboxylic acids or acid anhydrides is generally less satisfactory for producing higher carboxylates because of the difficulty of the reaction and the low yield obtained. Accordingly, it is an object of the present invention to provide a process for the preparation of higher carboxylates of silicon which uses readily available reactants and affords high yields of the desired carboxylate. It is another object of the invention to provide a method of preparation wherein the silicon tetracarboxylate produced is substantially free of deletrious impurities and has a high level of thermal stability. These and other objects, aspects and advantages of the present invention will become apparent to those skilled in the art from the following description of the invention.

SUMMARY OF THE INVENTION

This invention relates to a highly effective and efficient method of preparing higher silicon tetracarboxylates in high yield comprising the steps of reacting a lower silicon tetracarboxylate with at least one higher carboxylic acid at a temperature sufficiently high to vaporize and remove volatile material. In another embodiment of the invention, a stream of an inert gas is passed through the reaction mixture during the reaction. The resulting product is the silicon tetracarboxylate of said higher carboxylic acid.

DETAILED DESCRIPTION

According to the present invention, higher silicon tetracarboxylates are produced from higher carboxylic acids by reacting a lower silicon tetracarboxylate with at least one higher carboxylic acid, preferably at temperatures sufficiently high to vaporize and expel volatile by-products of the reaction, according to the following equation:

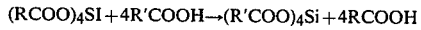

wherein R is an alkyl group having up to 4 carbon atoms and R' is an alkyl group having 5 to 24 or more carbon atoms.

The lower silicon tetracarboxylates which are preferably employed in the process of the invention include silicon tetraacetate, silicon tetrapropionate, silicon tetrabutyrate, silicon tetrapentanoate and mixtures thereof. Silicon tetraacetate is the especially preferred lower silicon tetracarboxylate. Typical higher carboxylic acids used in the process of the invention are those acids which have at least six carbon atoms. There is no criticality on the upper limit for the number of carbon atoms. The upper limit is dictated only by practicality. Desirably, R' in the equation of step (b) is alkyl having from five to about 24 carbon atoms. Preferably, R' is a straight- or branched-chain alkyl having seven to eleven carbon atoms. Preferred higher carboxylic acids include the branched-chain carboxylic acids, such as the neodecanoic acids and 2-ethylhexanoic acid. The higher carboxylic acid component may be a simple carboxylic acid or a mixture of two or more carboxylic acids.

As illustrated above by the equation of the reaction, the reaction by-product is the lower organic acid or acids. Thus, when silicon tetraacetate is a reactant, acetic acid would be the by-product when the higher carboxylic acid is reacted with the silicon tetraacetate. The lower organic acid by-product is desirably removed from the reaction environment in order to have the reaction equilibrium favor the formation of the higher silicon tetracarboxylate. Removal of the by-product lower acid can be achieved by distillation at elevated temperatures or under reduced pressure or by a combination of these techniques.

As indicated above, an inert gas is optionally passed through the reaction mixture during the reaction. It has been observed that the yield obtained in the process of the invention is considerably improved when the reaction is carried out in the presence of an inert gas. The means used for passing the inert gas through the mixture is not critical and any means for gas-liquid contact can be suitably used. One method of passing the inert gas through the reaction mixture is by bubbling the gas through the reaction mixture using a subsurface sparge. Inert gases useful in the invention are any gases which will not react with a component of the reaction mixture and which will not leave a possibly deleterious residual substance in the higher silicon tetracarboxylate product. Suitable inert gases include nitrogen, argon, helium, and neon. Mixtures of inert gases can also be used. Nitrogen is the preferred inert gas.

The flow rate of inert gas is not critical and its magnitude is limited by practical considerations. For example, the volatile by-product is generally removed by distillation, i.e., the vapors are condensed and removed. An excessive inert gas flow rate would overload the distillation condenser and thereby impede by-product removal as condensate. Furthermore, excessive flow rates could cause undesirable frothing of the reaction mixture. Suitable inert gas flow rates can easily be determined by those skilled in the art by balancing the gas flow rate against the physical effects to be avoided as a result of excessive flow. In general, gas flow rates of about 1 cu. ft./min. to about 20 cu. ft./min. are typical. Of course, reactor size and volume of the reaction mixture are also factors to be considered in determining an appropriate gas flow rate.

In carrying out the reaction the higher carboxylic acid is mixed with the lower silicon carboxylate and, while passing an inert gas through the reaction mixture if an inert gas is used, the temperature of the mixture is increased until the by-product lower organic acid is evolved as vapor. When silicon tetraacetate is a reactant evolution of acetic acid vapor is observed at a temperature of above about 150° C. The temperature is increased while maintaining the inert gas flow until the reaction is substantially complete, which will occur when the temperature reaches about 240° C. When the reaction is substantially complete, it is advantageous to reduce the pressure of the reaction to effect as complete removal as possible of by-product lower organic acid and to effect the desired degree of reaction completion. Of course, it is possible to conduct the reaction entirely under a subatmospheric pressure in addition to the passage of an inert gas through the mixture. The reaction pressure is not critical and its choice depends in part on the physical properties (e.g., boiling point) of the particular by-product species being removed. Thus, a convenient pressure can be easily determined by those having ordinary skill in the art.

The elevated temperature used to drive the reaction to completion also serves to eliminate unreacted higher carboxylic acid, which is also vaporized. At the completion of the reaction, the principal product of the reaction, i.e., the product remaining in the reactor, is the higher silicon tetracarboxylate essentially free of deleterious impurities. This product can be used as a hydrocarbon cracking catalyst passivator without further purification. Recovery of the product involves merely removing the silicon tetracarboxylate of the higher acid from the reactor after completion of the reaction.

The following examples further illustrate specific embodiments of the invention but are not to be considered as limiting the invention to the specifics involved. Parts and percentages are on a weight basis unless otherwise indicated.

EXAMPLE 1

A three neck reaction flask was equipped with a stirrer, a heating mantle and a reflux condenser attached to a Dean-Stark trap. The flask was charged with 15 grams of silicon tetraacetate and 32.73 grams of 2-ethyl hexanoic acid. With stirring, the reaction mixture was heated to 140° C. and maintained at that temperature for about 4 hours. At approximately 150° C. acetic acid evolved and was removed by distillation. Upon completion of the acetic acid evolution the reaction was terminated and the reactor contents cooled. The silicon tetra-2-ethyl hexanoate yield was determined to be 89.0%.

EXAMPLE 2

The procedure of Example 1 was repeated except that nitrogen was bubbled through the reaction mixture by means of a nitrogen purge. After atmospheric pressure acetic acid distillation ceased vacuum was applied for approximately one hour at 140° C. Upon completion of the reaction, the yield was determined to be 100.85% based on silicon. The theoretical silicon content of the desired product was calculated to be 4.67%. Analysis of the product of this example exploying tube excited X-ray fluorecense analysis (TEFA) gave results of 4.71%±0.05.

The foregoing examples illustrate the benefit obtained by the reaction of the invention. The reaction of EXAMPLE 1 was carried out without the use of an inert gas atmosphere. The yield obtained was 89%. EXAMPLE 2 illustrates the embodiment of the invention in which the reaction is carried out in the presence of nitrogen. Note that the yield was approximately stoichiometric.

Although the invention is described with particular reference to specific examples, it is understood that alternate embodiments may be employed. For example, silicon tetrapropionate may be used in place of the silicon tetraacetate. The scope of the invention is limited only by the breadth of the appended claims.

What is claimed is:

1. The method of producing higher tetracarboxylates of silicon comprising reacting a lower silicon tetracarboxylate with at least one higher carboxylic acid at a temperature sufficiently high to vaporize volatile material and recovering the silicon tetracarboxylate of said higher carboxylic acid.

2. The method of claim 1 wherein an inert gas is passed through the reaction mixture during the reaction.

3. The method of claim 2 wherein the inert gas is selected from the group consisting of nitrogen, helium, neon and argon.

4. The method of claim 1 wherein the higher carboxylic acid has the formula RCOOH wherein R is alkyl of at least six carbon atoms.

5. The method of claim 4 wherein the higher carboxylic acid is 2-ethylhexanoic acid.

6. The method of claim 4 wherein the higher carboxylic acid is neodecanoic acid.

7. The method of claim 4 wherein the higher carboxylic acid is a mixture of at least two acids.

8. The method of claim 7 wherein the higher carboxylic acid comprises a mixture of 2-ethylhexanoic acid and neodecanoic acid.

9. The method of claim 2 wherein the reaction is carried out at a temperature of about 100° C. to about 160° C.

10. The method of claim 9 wherein the volatile material removed comprises acetic acid.

11. The method of claim 1 wherein the reaction is carried out in the presence of a solvent.

12. The method of claim 11 wherein the solvent is a hydrocarbon having a boiling point of at least 100° C.

13. The method of claim 11 wherein the solvent is selected from the group consisting of toluene, cumene, xylene and kerosene.

* * * * *